(12) United States Patent
Vincent et al.

(10) Patent No.: US 10,643,746 B2
(45) Date of Patent: May 5, 2020

(54) IMAGE VIEWER

(71) Applicants: Brigil Vincent, Morrisville, NC (US); Tatsuo Kawanaka, Morrisville, NC (US); Keiichi Morita, Morrisville, NC (US); Prajeesh Prabhakaran, Morrisville, NC (US); Maneesh Chirangattu, Morrisville, NC (US)

(72) Inventors: Brigil Vincent, Morrisville, NC (US); Tatsuo Kawanaka, Morrisville, NC (US); Keiichi Morita, Morrisville, NC (US); Prajeesh Prabhakaran, Morrisville, NC (US); Maneesh Chirangattu, Morrisville, NC (US)

(73) Assignee: FUJIFILM MEDICAL SYSTEMS U.S.A., INC., Stamford, CT (US)

( * ) Notice: Subject to any disclaimer, the term of this patent is extended or adjusted under 35 U.S.C. 154(b) by 61 days.

(21) Appl. No.: 15/999,158

(22) Filed: Aug. 17, 2018

(65) Prior Publication Data
US 2020/0058388 A1 Feb. 20, 2020

(51) Int. Cl.
*A61B 5/00* (2006.01)
*G16H 30/40* (2018.01)
*G06T 1/20* (2006.01)
*G16H 30/20* (2018.01)
*G06T 1/60* (2006.01)
*A61B 6/00* (2006.01)

(52) U.S. Cl.
CPC .............. *G16H 30/40* (2018.01); *G06T 1/20* (2013.01); *G06T 1/60* (2013.01); *G16H 30/20* (2018.01); *G06T 2200/24* (2013.01)

(58) Field of Classification Search
CPC ................................. A61B 6/00; A61B 5/00
USPC .......... 382/131; 128/915; 378/4, 21, 37, 901
See application file for complete search history.

(56) References Cited

U.S. PATENT DOCUMENTS 8,923,594 B2 * 12/2014 Wehnes .................. G06T 7/143
382/132

* cited by examiner

*Primary Examiner* — Abolfazl Tabatabai
(74) *Attorney, Agent, or Firm* — Womble Bond Dickinson (US) LLP

(57) ABSTRACT

An image viewer and method for using the same in a medical image management system are described. In one embodiment, the system comprises: a network communication interface to receive compressed image pixel data; an image cache memory to cache the compressed DICOM image pixel data and rendered images; one or more processors coupled to the network connection interface and the memory and configured to implement an image rendering pipeline to perform image rendering in response to opening a healthcare study for review, wherein the image rendering includes determining whether compressed image pixel data associated with an image selected for display is in an image cache memory, and if so, then fetching the compressed image pixel data from an image cache, where the image pixel data represents a pre-rendered version of an image from a series in the healthcare study, and rendering a displayable image for display with a viewer on the display, and if not, then downloading from a remote location a version of the displayable image for display with the viewer; and a display coupled to the one or more processors to display the displayable image with a viewer.

20 Claims, 7 Drawing Sheets

Subscription
[1] Open study for review or trigger subscription
[1.1] Image Viewer places subscription request
[1.2] Enqueues subscription request based on priority
[1.3] Loader dequeues subscription request
[1.4] WADO request for compressed DICOM images
[1.5] Fetch DICOM pixel data
[1.6] Pre-render, optimize and apply compression
[1.7] Cache compressed DICOM images Rendering
[2] Interactive operation (eg: scroll, cine, windowing]
[2.1] Viewer places render request
[2.2] Enqueues render request
[2.3] Rendering Engine dequeues render request
[2.4] Decompress pre-rendered optimized DICOM image
[2.5] Process DICOM pixel data and convert to displayable image
[2.6] Pass displayable image to Image Viewer
[2.7] Draw displayable DICOM image

FIG. 4

IMAGE VIEWER

FIELD OF THE INVENTION

Embodiments of the present invention relate to the field of medical imaging analysis; more particularly, embodiments of the present invention relate to render locally and display medical images using cached compressed pixel data in low network speed environments.

BACKGROUND

Current medical imaging technology includes the use of medical images such as, among others, x-rays, mammograms, computerized tomography (CT) scans, magnetic resonance images (MRIs), positron emission tomography (PET) scans and ultrasound images. These images are generated by medical imaging modalities.

Medical facilities are more readily adopting electronic displays for displaying medical images. Often after an imaging modality takes medical images, those images are included in a study that is sent to a picture archiving and communication system (PACS). The PACS is a medical imaging technology that allows access to images from multiple locations. Doctors and/or other medical professionals obtain studies that are stored in the PACS and review, or read, the images in the studies to obtain clinical information about their patients. If a patient has a serious medical condition that needs urgent attention, the doctor is often able to make that determination by reviewing the images in the study.

Doctors and/or other medical professionals often view the images on workstation that has a display. To view the images from a study on the workstation, the images are rendered at a remotely-located server and then the rendered images are downloaded through a network for display on the workstation. The rendering of a particular image occurs in real-time in response to a request to view the image. The rendered image is downloaded through a network to workstation whose performance is largely dependent on network speed. Thus, if the network speed is low, then receipt of the rendered image is delayed. It is desirable to avoid such delays, particularly in cases where a doctor and/or other medical professional need to review the image immediately.

SUMMARY OF THE INVENTION

An image viewer and method for using the same in a medical image management system are described. In one embodiment, the system comprises: a network communication interface to receive compressed image pixel data; an image cache memory to cache the compressed DICOM image pixel data and rendered images; one or more processors coupled to the network connection interface and the memory and configured to implement an image rendering pipeline to perform image rendering in response to opening a healthcare study for review, wherein the image rendering includes determining whether compressed image pixel data associated with an image selected for display is in an image cache memory, and if so, then fetching the compressed image pixel data from an image cache where the image pixel data represents a pre-rendered version of an image from a series in the healthcare study, decompressing the compressed image pixel data to obtain the image pixel data, performing one or more image processing operations on the image pixel data, generating a displayable image from the image pixel data that has undergone image processing, and rendering the displayable image for display with a viewer on the display, and if not, then downloading from a remote location a version of the displayable image for display with the viewer; and a display coupled to the one or more processors to display the displayable image with a viewer.

BRIEF DESCRIPTION OF THE DRAWINGS

The present invention will be understood more fully from the detailed description given below and from the accompanying drawings of various embodiments of the invention, which, however, should not be taken to limit the invention to the specific embodiments, but are for explanation and understanding only.

FIG. 4 illustrates an operations list for image request and rendering for one embodiment of a medical image management system.

DETAILED DESCRIPTION

In the following description, numerous details are set forth to provide a more thorough explanation of the present invention. It will be apparent, however, to one skilled in the art, that the present invention may be practiced without these specific details. In other instances, well-known structures and devices are shown in block diagram form, rather than in detail, in order to avoid obscuring the present invention.

Embodiments of the present invention are directed to systems, methods, and GUIs for rendering and displaying medical, or healthcare, images, particularly in low network speed environments. The systems, methods, and GUIs of the present invention not only have the ability to cache compressed image pixel data (e.g., DICOM image pixel data) and render images locally instead of relying on server-side rendering of images when the low network speed would unnecessarily delay generation and display of such images. Having briefly described an overview of the present invention, embodiments of the invention will be discussed with reference to FIGS. 1-7.

The subject matter of embodiments of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies.

Having briefly described embodiments of the present invention, an exemplary operating environment suitable for use in implementing embodiments of the present invention is described below.

Figure 1:
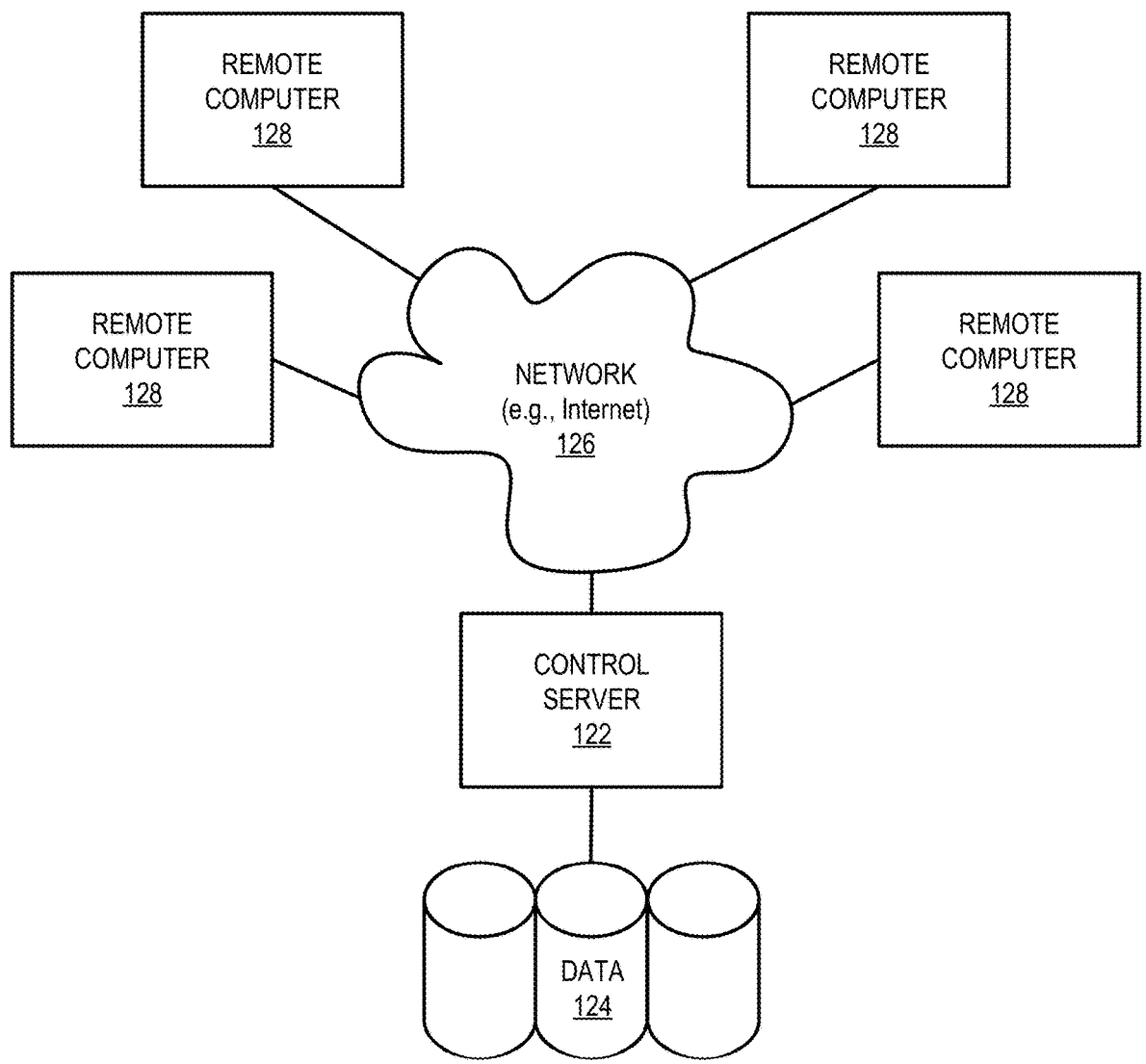
FIG. 1 illustrates an exemplary a medical information computing system environment, with which embodiments of the present invention may be implemented.

Referring to the drawings in general, and initially to FIG. 1 in particular, a medical information computing system environment, with which embodiments of the present invention may be implemented is illustrated and designated generally as reference numeral 120. It will be understood and appreciated by those of ordinary skill in the art that the illustrated medical information computing system environment 120 is merely an example of one suitable computing environment and is not intended to suggest any limitation as to the scope of use or functionality of the invention. Neither should the medical information computing system environment 120 be interpreted as having any dependency or requirement relating to any single component or combination of components illustrated therein.

Embodiments of the present invention may be operational with numerous general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, programmable consumer electronics, network PCs, minicomputers, mainframe computers, distributed computing environments that include any of the above-mentioned systems or devices, and the like.

Embodiments of the present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in association with local and/or remote computer storage media including, by way of example only, memory storage devices.

With continued reference to FIG. 1, the exemplary medical information computing system environment 120 includes a general purpose computing device in the form of a control server 122. Components of the control server 122 may include, without limitation, a processing unit, internal system memory, and a suitable system bus for coupling various system components, including database cluster 124, with the control server 122. The system bus may be any of several types of bus structures, including a'memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 122 typically includes therein, or has access to, a variety of computer-readable media, for instance, database cluster 124. Computer-readable media can be any available media that may be accessed by server 122, and includes volatile and nonvolatile media, as well as removable and non-removable media. By way of example, and not limitation, computer-readable media may include computer storage media. Computer storage media may include, without limitation, volatile and nonvolatile media, as well as removable and non-removable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 122. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including database cluster 124, provide storage of computer-readable instructions, data structures, program modules, and other data for the control server 122. The control server 122 may operate in a computer network 126 using logical connections to one or more remote computers 128. Remote computers 128 may be located at a variety of locations in a medical or research environment, for example, but not limited to, clinical laboratories (e.g., molecular diagnostic laboratories), hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as intensivists, surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, genetic counselors, researchers, veterinarians, students, and the like. The remote computers 128 may also be physically located in non-traditional medical care environments so that the entire health care community may be capable of integration on the network. The remote computers 128 may be personal computers, servers, routers, network PCs, peer devices, other common network nodes, or the like, and may include some or all of the elements described above in relation to the control server 122. The devices can be personal digital assistants or other like devices.

Exemplary computer networks 126 may include, without limitation, local area networks (LANs) and/or wide area networks (WANs). Such networking environments are commonplace in offices, enterprise-wide computer networks, intranets, and the Internet. When utilized in a WAN networking environment, the control server 122 may include a modem or other means for establishing communications over the WAN, such as the Internet. In a networked environment, program modules or portions thereof may be stored in association with the control server 122, the database cluster 124, or any of the remote computers 128. For example, and not by way of limitation, various application programs may reside on the memory associated with any one or more of the remote computers 128. It will be appreciated by those of ordinary skill in the art that the network connections shown are exemplary and other means of establishing a communications link between the computers (e.g., control server 122 and remote computers 128) may be utilized.

In operation, a clinician may enter commands and information into the control server 122 or convey the commands and information to the control server 122 via one or more of the remote computers 128 through input devices, such as a keyboard, a pointing device (commonly referred to as a mouse), a trackball, or a touch pad. Other input devices may include, without limitation, microphones, scanners, or the like. Commands and information may also be sent directly from a remote healthcare device to the control server 122. In addition to a monitor, the control server 122 and/or remote computers 128 may include other peripheral output devices, such as speakers and a printer.

Although many other internal components of the control server 122 and the remote computers 128 are not shown, those of ordinary skill in the art will appreciate that such components and their interconnection are well known. Accordingly, additional details concerning the internal construction of the control server 122 and the remote computers 128 are not further disclosed herein.

Figure 2:
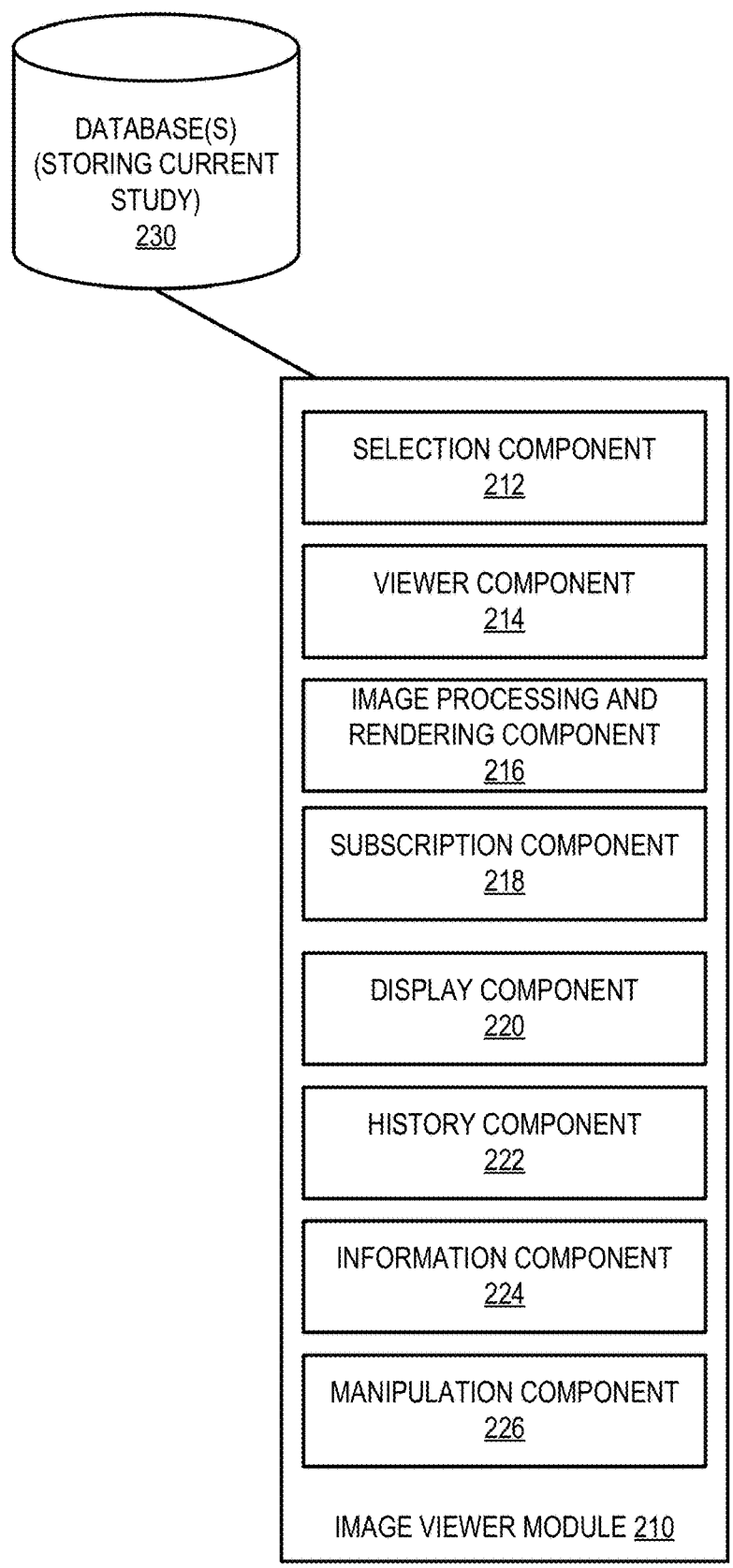
FIG. 2 is a block diagram showing one embodiment of a computing system architecture for displaying series images in a graphical user interface (GUI).

With reference to FIG. 2, a block diagram is illustrated that shows an exemplary computing system architecture for seamless viewing of medical images (e.g., DICOM images) in a low network speed environment by locally rendering images using compressed image pixel data cached locally. It will be appreciated that the computing system architecture shown in FIG. 2 is merely an example of one suitable computing system and is not intended as having any dependency or requirement related to any single module/component or combination of modules/components.

The computing system includes an image viewer 210 and one or more databases 230, storing and maintaining medical images from image series of multiple healthcare studies. Exemplary medical images include radiology images, laboratory images, pictures, cardiology images, such as ECHO images, and other healthcare images. One of skill in the art will appreciate that the databases may be maintained separately or may be integrated. Databases 230 may contain images that are linked to a patient's electronic medical record (EMR), such that images may be selected from within the EMR and launched and displayed within a viewer via the image viewer 210. As utilized herein, the acronym "EMR" is not meant to be limiting, and may broadly refer to any or all aspects of the patient's medical record rendered in a digital format. Generally, the EMR is supported by systems configured to co-ordinate the storage and retrieval of individual records with the aid of computing devices. As such, a variety of types of healthcare-related information may be stored and accessed in this way. By way of example, the EMR may store one or more of the following types of information: patient demographic; medical history (e.g., examination and progress reports of health and illnesses); medicine and allergy lists/immunization status; laboratory test results, radiology images (e.g., X-rays, CTs, MRIs, etc.); other images; evidence-based recommendations for specific medical conditions; a record of appointments and physician's notes; billing records; and data received from an associated medical device. Accordingly, systems that employ EMRs reduce medical errors, increase physician efficiency, and reduce costs, as well as promote standardization of healthcare. Display component 220 includes a graphical display device that may be a monitor, computer screen, project device or other hardware device for displaying output capable of displaying graphical user interfaces.

Image viewer 210 receives and displays images that are sourced from more than one source, or database. Thus, a single storage repository or a single PACS system is not required. Image viewer 210 may reside on one or more computing devices, such as, for example, the control server 22 described above with reference to FIG. 1. By way of example, the control server 22 includes a computer processor and may be a server, personal computer, desktop computer, laptop computer, handheld device, mobile device, consumer electronic device, or the like.

Image viewer 210 comprises selection component 212, viewer component 214, image processing and rendering component 216, subscription component 218, and display component 220. In various embodiments, image viewer 210 includes a history component 222, an information component 224, and a manipulation component 226. It will be appreciated that while image viewer 210 is depicted as receiving healthcare images from a current study stored in database 230, image viewer 210 may receive healthcare images from multiple sources including databases spread across multiple facilities and/or multiple locations. It will also be appreciated that image viewer 210 may receive healthcare images from the sources described above via links within a patient's EMR.

The selection component 212 receives a selection of a healthcare study. A healthcare study comprises one or more series. Each series comprises one or more images depicting the subject of the image from various angles. A list perspective within a multimedia manager provides a list of available studies, images, and other media. A clinician can select the desired items to launch in the viewer. In one embodiment, the selection of desired items may be made within the EMR.

Once the selection component 212 receives the clinician's selection, the viewer component 214 launches the viewer for the selected studies. The image processing and rendering component 216 access compressed image pixel data associated with at least one image selected for presentation from local storage (e.g., a local image cache), decompressed the image pixel data, performs one or more image processing operations (if desired or necessary), and renders the image.

If the compressed image pixel data is not available, subscription component 218 controls the requesting of the compressed image pixel data from a remote location (e.g., a remotely-located server), receives the data and has it stored locally. In one embodiment, subscription component 218 obtains the compressed based on a prioritized subscription order. Thereafter, image processing and rendering component 216 generates and renders a displayable image from the compressed image pixel data.

The display component 220 displays the one or more images of the current study in the viewer.

In one embodiment, a history component 222 displays a history of different studies and clinical images associated with the more than one healthcare image. The history component 222 further allows a selection of one or more images from the history to be displayed in the viewer by the display component 220. For example, the selection component 212 may have received a selection from the clinician of a particular study. However, once the display component 220 has displayed the images that comprise that selected study, the history component 222 may display other studies and clinical images that are of particular interest to the clinician. The clinician may then select additional items from the history to launch within the viewer.

In one embodiment, information component 224 displays additional information associated with the more than one healthcare image, the history, or a combination thereof. The additional information comprises patient identifying information, image related information, study related information, or a combination thereof. Such additional information may also include time related information.

In one embodiment, a manipulation component 226 allows a clinician to manipulate a display of a healthcare image. For example, a clinician may determine that the image as it is rendered within the viewer is not large enough to see a desired level of detail. The clinician may zoom in or out and the manipulation component 226 manipulates the display of the image accordingly. Similarly, the clinician may desire to pan an image and the manipulation component 226 manipulates the image display accordingly.

Figure 3:
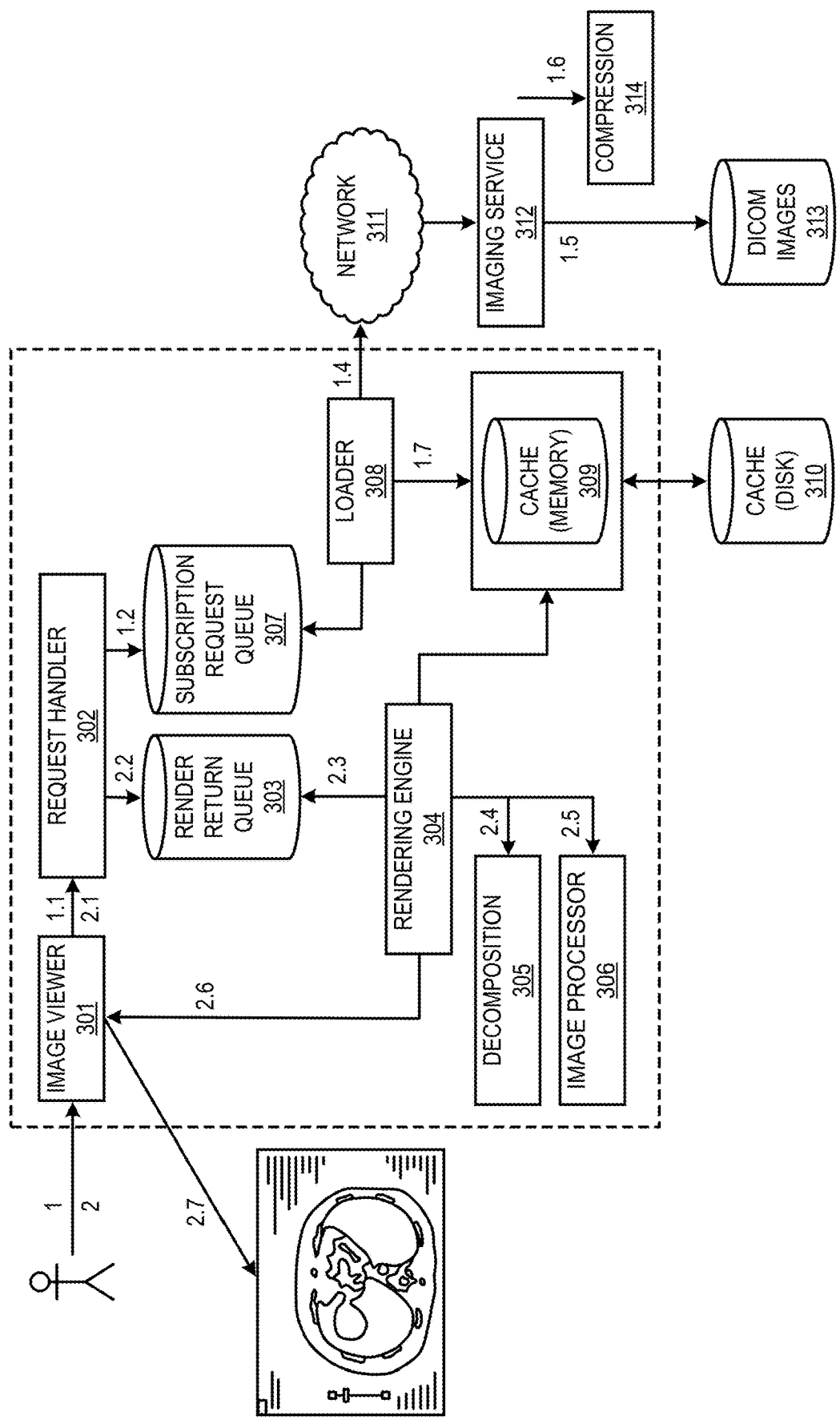
FIG. 3 is a data flow diagram of one embodiment of a process for image rendering being performed with a medical image management system.

FIG. 3 is a data flow diagram of one embodiment of a process for image rendering being performed with a medical image management system. The medical image management system performs image rendering and viewing to create a layout in the GUI with at least one image from one image series of the current study. In one embodiment, the medical image management system provides seamless viewing of medical images (e.g., DICOM images) in low network speed environment by caching compressed image pixel data in the system and rendering images locally. In one embodiment, the system is implemented with one of the viewers of FIG. 2 or the system of FIG. 7.

In one embodiment, the medical image management system comprises a network communication interface to receive compressed image pixel data; an image cache memory to cache the compressed DICOM image pixel data and rendered images; and one or more processors coupled to the network connection interface and the memory are configured to implement an image rendering pipeline to perform image rendering in response to opening a healthcare study for review, and a display coupled to the one or more processors to display the displayable image with a viewer (e.g., a browser window being displayed on a display of the medical image management system). In one embodiment, the medical image management system comprises a workstation.

In one embodiment, the image rendering includes determining whether compressed image pixel data associated with an image selected for display is in an image cache memory, and if so, then fetching the compressed image pixel data from an image cache, the image pixel data representing a pre-rendered version of an image from a series in the healthcare study, decompressing the compressed image pixel data to obtain the image pixel data, performing one or more image processing operations on the image pixel data, generating a displayable image from the image pixel data that has undergone image processing, and rendering the displayable image for display with a viewer on the display.

If the compressed image pixel data associated with an image selected for display is not in an image cache memory, then downloading from a remote location a rendered version of the displayable image for display with the viewer. That is, server-side rendering is utilized only if the image is not available in the image cache. In one embodiment, the processor requests the compressed image pixel data from a server remotely located with respect to the system via the network connection and download the compressed image pixel data into the image cache.

Thus, the processor requests the compressed image pixel data from an image cache preferably over requesting the compressed image pixel data from a server remotely located from the server in order to compensate for a low network speed environment in which network speed is below a threshold. In other words, depending on the network speed, other compressed image data associated with images in the series/study being viewed are downloaded and stored in the cache so that they may be rendered locally.

Note that in one embodiment, when a study is initially opened and the first image from the study is selected for display, the image to be viewed can be either rendered from server or client depending upon whether that image cached already or not.

Referring to FIG. 3, in one embodiment, the process for image rendering being performed with the medical image management system has two logical parts:

1) Subscription: Cache compressed medical image pixel data in the system.

2) Rendering: Decompress medical image pixel data and render displayable images One embodiment of the operations associated with part is depicted in FIG. 4.

Referring both FIGS. 3 and 4, the subscription part of the process is triggered when opening a new study in image viewer 301 (e.g., a browser window) or user triggers subscription from scheduled worklist. In one embodiment, the subscription is only triggered in a case where a study is opened and the system doesn't already have the compressed image pixel data stored locally. If the data is available locally, the system renders the image with the local data.

In one embodiment, the worklist may include a number of studies that have been sent to an individual for review and have been designated for download to the system from remotely located storage.

Upon triggering subscription, image viewer 301 generates a request for receiving the pre-rendered, optimized and compressed DICOM image pixel data to imaging service 312 running on a remotely-located server so that the compressed DICOM image pixel data can be download to workstation cache. In one embodiment, the following optimizations are performed. First, pre-rendering of the image is performed. In one embodiment, pre-rendering includes parsing the DICOM image and select display attributes from metadata. Second, in one embodiment, if the image requires non-linear transformation based on histogram, this will be done as part of pre-rendering in order to avoid having this processing performed on the client side. Third, in one embodiment, pre-rendering also includes separating pixel data from metadata and combining pixel with required display properties. Fourth, in one embodiment, compression is applied in an efficient manner in such a way to reduce its download time and also by reducing its decompression time. This helps faster download in low networks. In one embodiment, workstation cache comprises a combination of memory cache 309 and disk cache 310 in such a way that, when memory cache 309 reaches a configured limit, the cache is extended to workstation disk cache 310.

Image viewer 301 sends the request to request handler 302 that queues the request in subscription request queue 307. In one embodiment, the request is queued based on priority. That is, the subscription download order is based on priority. In one embodiment, DICOM images of the series selected for display in image viewer 301 always get higher priority and they will be cached first compared to image data associated with images of other series in the study.

In one embodiment, a user can change reading protocol and display layout, a toolbar component associated with the viewer displays multiple reading protocols and layouts applicable for the study being displayed, so that user can change display layouts anytime. In one embodiment, changing reading protocols or display layouts or switching series will cause changes to the subscription priority to occur dynamically. More specifically, the use of subscription is handled at the series level with each subscription request representing a series in the study. In one embodiment, when performing subscription of a study that has, for example, ten series where the first four series have to be displayed based on reading protocol, ten subscription requests are generated with the first four requests having a higher priority compared to rest of the requests. When the user changes the reading protocol during subscription, the priority in existing subscription list is updated to reflect the change in reading protocol/display layout in such a way that the series to be displayed get a higher priority and their images are cached first. Similarly, if a user drags and drops a specific random series from a series picker to a viewport, the priority of the subscription request corresponding to that series becomes higher.

Loader 308 takes each request from subscription request 307 and sends it via a network interface of the system over network 311 (e.g., the Internet). In one embodiment, loader 308 sends the request as a Web Access to DICOM Objects (WADO) request. Imaging server 312 at a remotely located server receives the request from network 311 and fetches the DICOM image pixel data from DICOM image storage 313.

After fetching the DICOM image pixel data, imaging server 312 performs pre-rendering, optimizes the image pixel data and applies compression to the image pixel data. In one embodiment, the pre-rendering includes separating the image pixel data from some metadata in the DICOM image file. Some of the metadata is removed, while others associated with windowing, slope/intercept, image width and height, SUV type, SUV windowing, interpolation, shutter, mask, softcopy VOI LUT, displayed area, pixel spacing, spatial transformation, photometric interpretation, etc., are kept with the pixel image data. This remaining metadata will be used for rendering the image locally. In one embodiment, the compression that is applied to reduce download time and reduce subsequent decompression time, thereby facilitating faster download in low networks, is the compression described in U.S. Pat. No. 7,183,950. In another embodiment, the compression that is applied is the compression described in U.S. Pat. No. 7,773,820, both of which are incorporated herein by reference. Note that other compression techniques that are well-known in the art may be used.

After performing the pre-rendering, any optimizations, and compressed, imaging service 312 sends the compressed DICOM image pixel data back to the management system via network 311 where it is received by the management system's network interface and cached in the image cache. At this point, the compressed DICOM image pixel data could be decompressed and an image rendered from the DICOM image pixel data.

In one embodiment, the system displays a progress indicator (e.g. status bar) in the viewport where image is being displayed indicating progress of the subscription. When the data has been completely downloaded and the caching is completed for the series, the progress bar display disappears.

Note that if the request is for the first image in the series, imaging service 312 may provide a fully rendered version of the image selected for viewing while providing compressed DICOM image pixel data for the other images in the series. This may allow a user to avoid some additional delay in viewing the images from the series.

During image rendering, image viewer 301 fetches compressed DICOM images from cache 309, decompress images using decompressor 305 to DICOM image pixel data, perform image processing on decompressed DICOM image pixel data using image processor 306 and generates a final displayable image which will be displayed in image viewer 301.

As part of a hybrid approach, when images are not cached yet, image viewer 301 will rely on server-side rendering to display images, by sending WADO (Web Access to DICOM Objects) request to imaging service 312 to retrieve rendered displayable DICOM images. In such cases, the user doesn't require to wait for all images to be stored in workstation cache to proceed with interactive operations in image viewer. In one embodiment, such requests are not queued and are sent via request handler 302 and loader 308 immediately to imaging service 312. Also, in one embodiment, the request indicates that a fully rendered image(s) is requested as opposed to the compressed image pixel data.

In one embodiment, the rendering process begins by the user performing interactive operations with image viewer 301, which image viewer 301 recognizes and performs operations in response thereto. Examples of interactive operations include zoom, pan, windowing, rotate, flip, various types of image scrolling, cine, mask, shutter, image magnification, color table operations, etc. In this way, the system is able to perform operations on the original DICOM pixel image data (that has been pre-rendered by imaging service 312).

In response to an interactive operation, image viewer 301 places a render request into render request queue 303, via request handler 302, where the request is stored. Renderer 304 dequeues the request, obtains the compressed pre-rendered optimized image pixel data from image cache 309, performs decompression on the pre-rendered optimized DICOM image data using decompressor 305, processes the DICOM pixel data using image processor 306, and converts the processed pixel data to a displayable image with renderer 304. Renderer 304 passes the displayable image to image viewer 301, which draws the displayable DICOM image on the display of the system. Decompression performed by decompressor 305 is to reverse the compression 314 performed by imaging service 312. Note that image processing operations performed by image processor 305 are to implement the interactive operations may with respect to image viewer 301.

Figure 5:
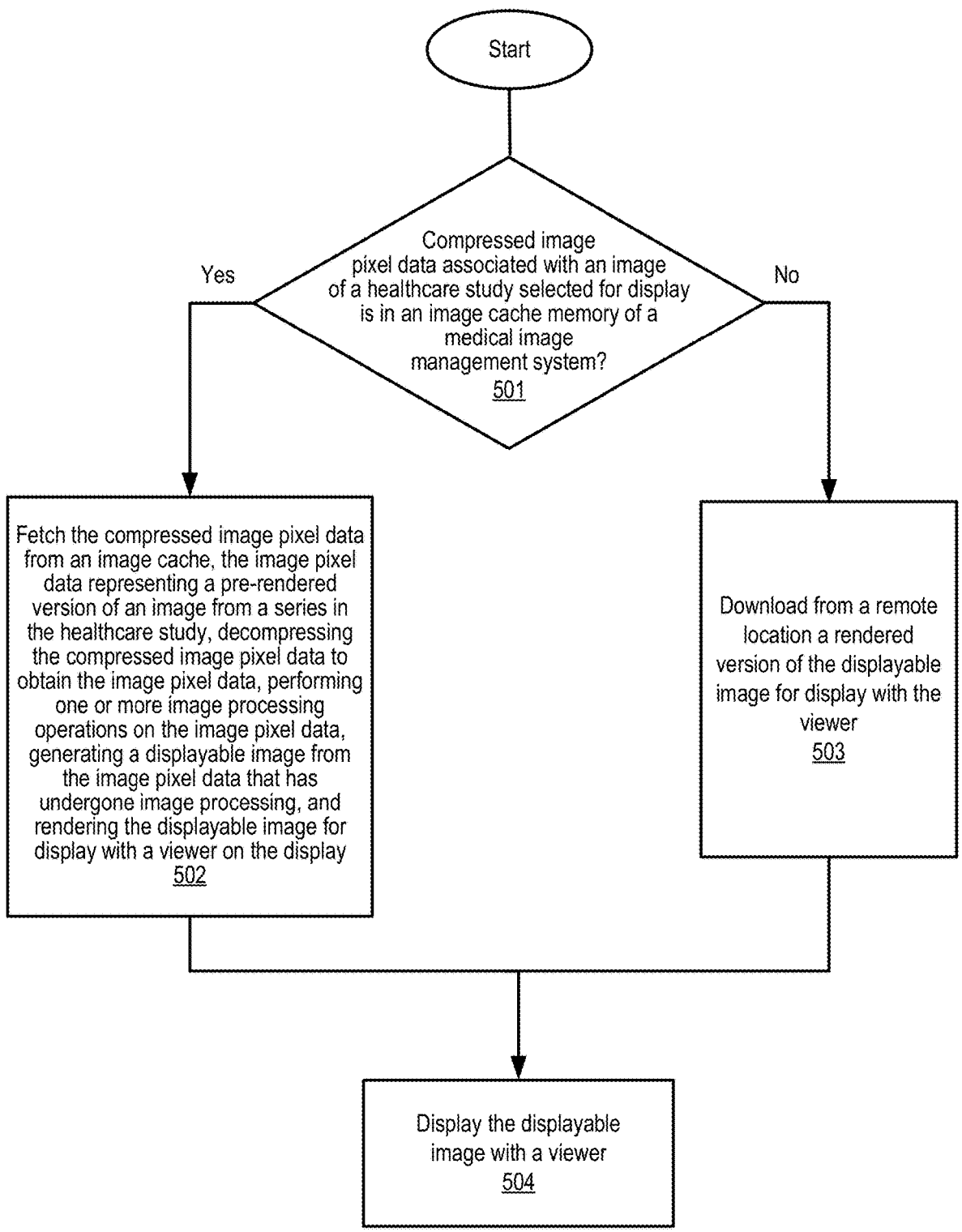
FIG. 5 is a flow diagram of one embodiment of a process for displaying series images in a graphical user interface (GUI).

FIG. 5 is a flow diagram of one embodiment of a process for displaying series images in a graphical user interface (GUI). In one embodiment, the processes are performed by processing logic that may comprise hardware (circuitry, dedicated logic, etc.), software (e.g., software running on a chip), firmware, or a combination of the three. In one embodiment, the process is performed by a medical image management system having an image processor, an image renderer, and a display.

Referring to FIG. 5, the process begins by processing logic determining whether the compressed image pixel data associated with an image of a healthcare study selected for display is in an image cache memory of a medical image management system (processing block 501). If it is, then the process transitions to processing block 502 where processing logic fetches the compressed image pixel data from an image cache. In one embodiment, as described above, the image pixel data representing a pre-rendered version of an image from a series in the healthcare study.

After fetching the compressed image pixel data, processing logic decompresses the compressed image pixel data to obtain the image pixel data, performs one or more image processing operations on the image pixel data, generates a displayable image from the image pixel data that has undergone image processing, and renders the displayable image for display with a viewer on the display. In one embodiment, the one or more operations include windowing, cine, zooming, panning, window leveling, and other well-known image processing operations performed on medical images during their review.

If the compressed image pixel data associated with an image selected for display is not in an image cache memory, then the process transitions to processing block 503 where processing logic downloads, from a remote location (e.g., a remotely located server) a rendered version of the displayable image for display with the viewer.

Thereafter, processing logic displays the displayable image with a viewer of the medical image management system (processing block 504).

Figure 6:
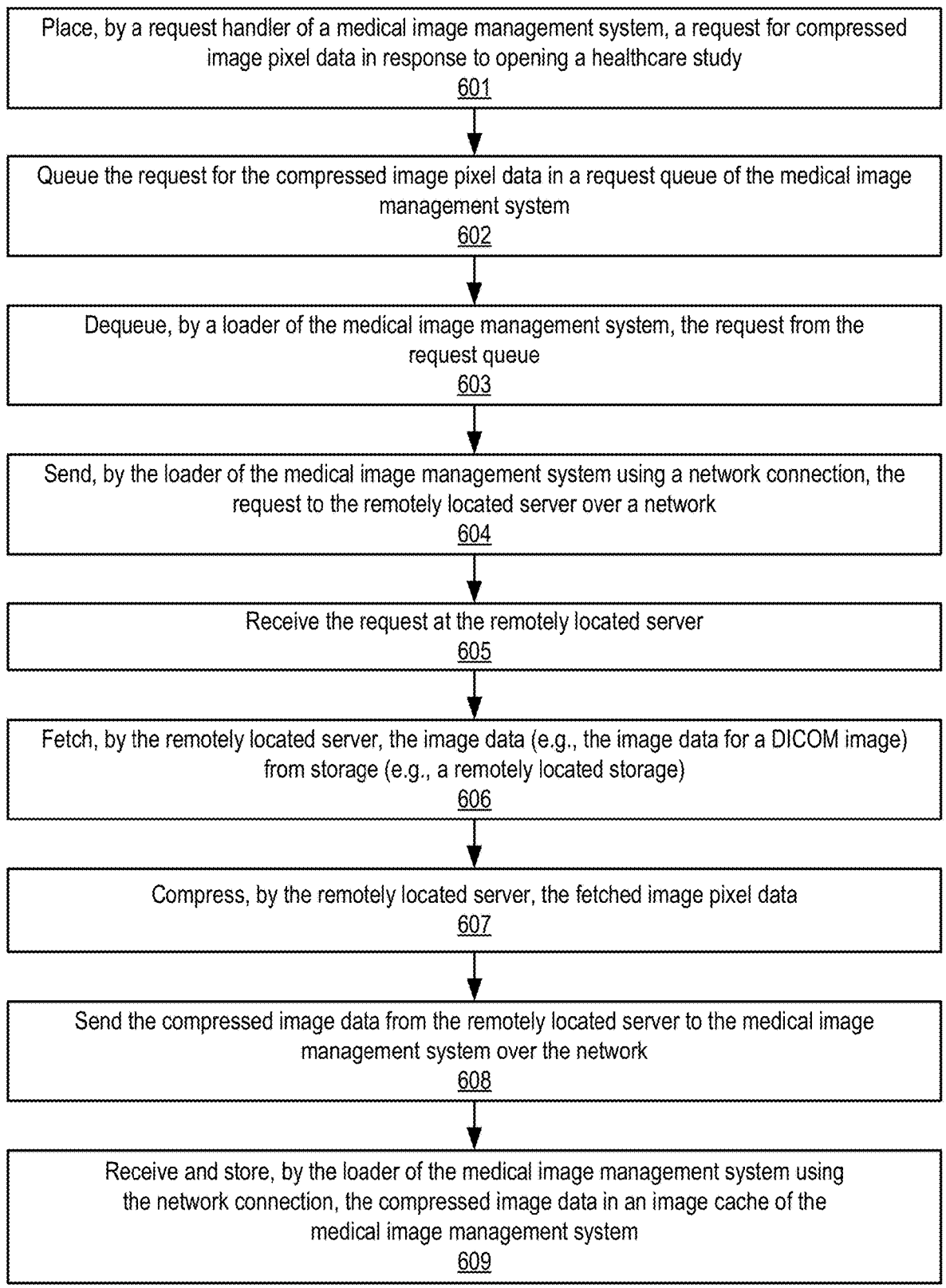
FIG. 6 is a flow diagram of one embodiment of a process for requesting compressed image pixel data from a server remotely located with respect to the system and downloading the compressed image pixel data into the image cache.

FIG. 6 is a flow diagram of one embodiment of a process for requesting compressed image pixel data from a server remotely located with respect to the system via the network connection and download the compressed image pixel data into the image cache. In one embodiment, the processes are performed by processing logic that may comprise hardware (circuitry, dedicated logic, etc.), software (e.g., software running on a chip), firmware, or a combination of the three. In one embodiment, the process is performed by a medical image management system having an image loader and an image cache.

Referring to FIG. 6, the process begins by processing logic generating a request for compressed image pixel data in response to opening a healthcare study (processing block 601). In one embodiment, the processing logic to place the request for the compressed image pixel data is part of a request handler of a medical image management system.

After generating the request, processing logic queues the request for the compressed image pixel data in a request queue of the medical image management system (processing block 602). Note that there may be a number of requests that are queued in the queue. These requests may be handled in the order in which they were stored in the queue. In another embodiment, the requests are handled based on priority. In one embodiment, the priority is controlled by subscription logic of the medical image management system.

Subsequently, processing logic dequeues the request from the request queue (processing block 603). In one embodiment, the processing logic to dequeue the request for the compressed image pixel data is part of a loader of a medical image management system.

Processing logic sends the dequeued request to the remotely located server over a network using a network interface of the medical image management system (processing block 604). In one embodiment, the request is sent over the Internet to the remote server that has access to the images that is to be rendered.

Processing logic of the server receives the request (processing block 605), fetches the image data (e.g., the image data for a DICOM image) from storage (e.g., a remotely located storage) (processing block 606), compresses the fetched image pixel data (processing block 607), and then sends the compressed image data from the remotely located server to the medical image management system over the network (processing block 608).

Processing logic of the medical image management system receives the compressed image pixel data and stores it in an image cache of the medical image management system (processing block 609). In one embodiment, the loader of the medical image management system using the network connection receives and stores the compressed image pixel data.

An Exemplary Medical Imaging Management System

Figure 7:
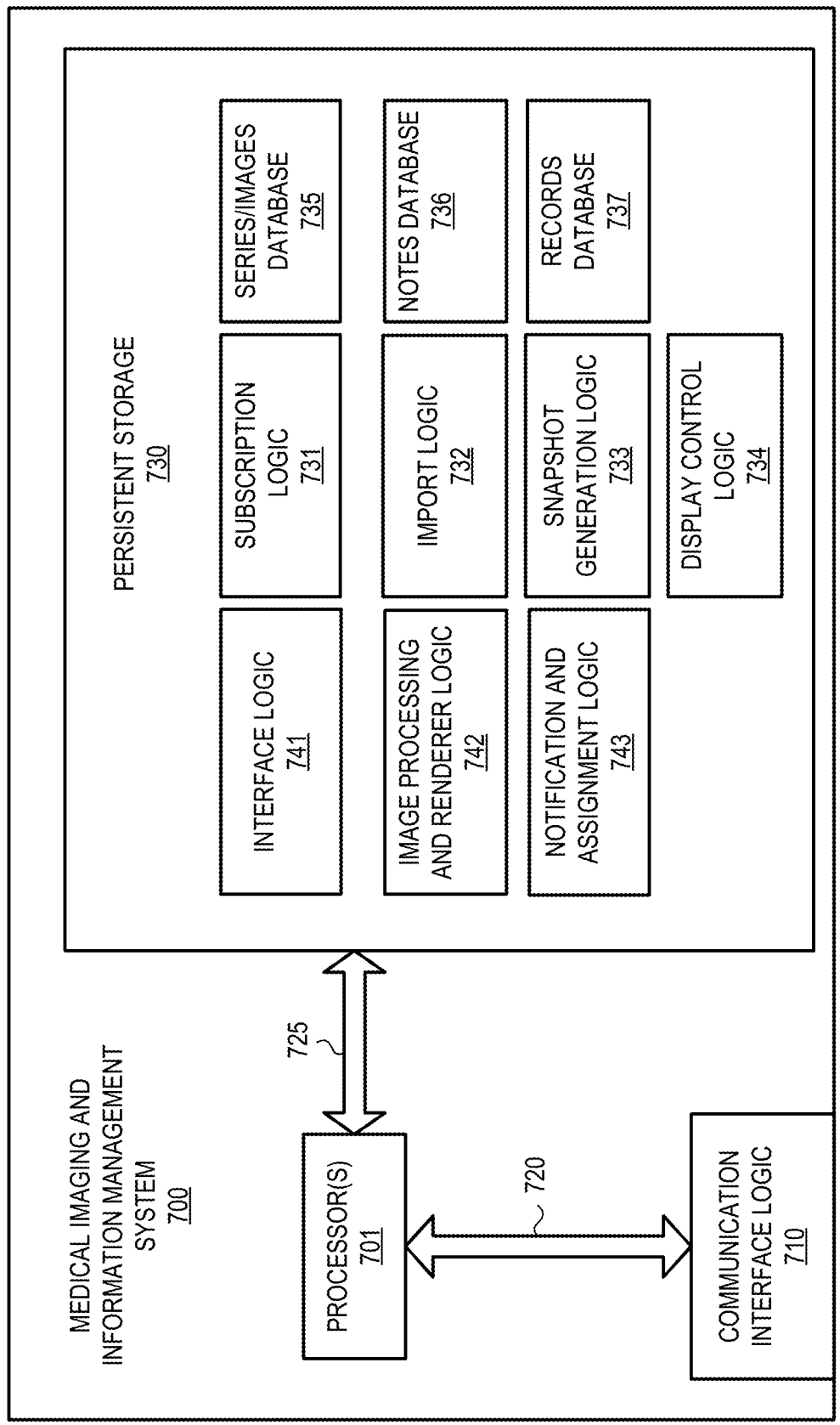
FIG. 7 illustrates an exemplary embodiment of a logical representation of a medical imaging and information management system that generates and renders images from healthcare studies.

FIG. 7 illustrates an exemplary embodiment of a logical representation of a medical imaging and information management system 700 that generates and renders image comparison layouts discussed above. The system performs matching of image series based on image similarity and automatically creates layouts with series images of a current study and one or more past (previously-created) studies. In one embodiment, system 700 is part of a medical image system such as detailed above.

The medical imaging and information management system 700 includes one or more processors 701 that are coupled to communication interface logic 710 via a first transmission medium 720. The communication interface logic 710 enables communications with other electronic devices, specifically enabling communication with remote users such as doctors, nurses and/or medical technicians, remote databases (e.g., PACS) that store healthcare studies, and healthcare modalities that generate and send studies. According to one embodiment of the disclosure, communication interface logic 710 may be implemented as a physical interface including one or more ports for wired connectors. Additionally, or in the alternative, communication interface logic 710 may be implemented with one or more radio units for supporting wireless communications with other electronic devices.

The processor(s) 701 is further coupled to persistent storage 730 via transmission medium 725. According to one embodiment of the disclosure, persistent storage 730 may include (a) user interface logic 741, (b) image processing and rendering logic 742, (c) notification and assignment logic 743, (d) subscription logic 731, (e) an import logic 732, (f) a snapshot generation logic 733, (g) a display control logic 734, (h) an images database 735, (i) a notes database 736 and (j) a records database 737.

The user interface logic 741 may include logic for enabling interaction between a user and the display areas being displayed on the screen.

The image processing and rendering logic 742 includes logic for requesting images to be rendered and rendering the images from compressed image pixel data as described above. In one embodiment, the image processing and rendering logic 742 performs one or more image processing operations on the image data, such as, for example, those described above.

The subscription logic 731 includes logic for caching compressed image pixel data (e.g., DICOM image pixel data from DICOM images) in the medical imaging and information management system 700. In one embodiment, the subscription logic 731 is triggered in response to opening a new study in an image viewer of the medical imaging and information management system 700. In one embodiment, the subscription logic 731 is also be triggered from scheduled worklist. In one embodiment, the subscription logic 731 obtains the compressed based on a prioritized subscription order. In one embodiment, the subscription order is based on priority such that images under which the series selected to display in the viewer of the medical imaging and information management system 700 get higher priority and are cached first compared to other series in the study. In one embodiment, the subscription logic 731 is responsive to changes in the reading protocols, display layouts or series switches and makes changes to the subscription priority dynamically. In one embodiment, the subscription logic 731 generates a progress indicator for display in the viewer indicating the progress of the subscription download process.

The notification and assignment logic 743 includes logic to issue and send notifications and/or assignments for study reviews.

The import logic 732 may include logic for retrieving one or more pieces of information from a storage device and importing each of the one or more pieces of information into a separate display area of a viewer or viewer template. For example, the pieces of information may include, but are not limited or restricted to, (i) medical images, including x-rays, mammograms, computerized tomography (CT) scans, magnetic resonance imaging (MRI), positron emission tomography (PET) scan and/or ultrasound imaging, (ii) physician's notes regarding one or more of the medical images and/or (iii) medical records corresponding to one or more of the subjects of the one or more medical images.

The snapshot generation logic 733 includes logic for saving at least a first state of the layout template. Saving the first state may include storing, at least, (i) the one or more pieces of information, and (ii) viewing properties of each of the one or more pieces of information in a non-transitory computer-readable medium. The layout template may depict a comparison layout depicting one or more images from a current study and one or more images determined to be similar from one or more previously-created studies.

The display control logic 734 includes logic for displaying images that have been rendered locally from the compressed image pixel data or have been rendered server-side and sent from the server in displayable form. In one embodiment, the display control logic 734 includes logic to display a browser into which the images are displayed.

The images database 735, the notes database 736 and the records database 737 may comprise a single non-transitory computer-readable medium storage device or may each be a separate non-transitory computer-readable medium storage device. The images database 735 stores medical images that a user may import into a display area of a viewer or other GUI. The notes database 736 stores notes recorded by a doctor, nurse, medical technician, etc., that a user may import into a display area of a layout template. Finally, the records database 737 stores medical records that a user may import into a display area of a layout template.

There is a number of example embodiments described herein.

Example 1 is a system comprising: a network communication interface to receive compressed image pixel data; an image cache memory to cache the compressed DICOM image pixel data and rendered images; one or more processors coupled to the network connection interface and the memory and configured to implement an image rendering pipeline to perform image rendering in response to opening a healthcare study for review, wherein the image rendering includes determining whether compressed image pixel data associated with an image selected for display is in an image cache memory, and if so, then fetching the compressed image pixel data from an image cache, the image pixel data representing a pre-rendered version of an image from a series in the healthcare study, decompressing the compressed image pixel data to obtain the image pixel data, performing one or more image processing operations on the image pixel data, generating a displayable image from the image pixel data that has undergone image processing, and rendering the displayable image for display with a viewer on the display, and if not, then downloading from a remote location a version of the displayable image for display with the viewer; a display coupled to the one or more processors to display the displayable image with a viewer.

Example 2 is the system of example 1 that may optionally include that the processor is further operable to request compressed image pixel data from a server remotely located with respect to the system via the network connection and download the compressed image pixel data into the image cache.

Example 3 is the system of example 3 that may optionally include that the processor is further operable to: generate and queue the request in response to the healthcare study being opened; send, using a loader, the request to the remotely located server; and receive and store in the image cache the compressed image pixel data received from the remotely located server.

Example 4 is the system of example 3 that may optionally include that the processor requests the compressed image pixel data from the server in response to determining the compressed image pixel data is not stored in the image cache.

Example 5 is the system of example 4 that may optionally include that the compressed image pixel data is requested by the processor based on a priority.

Example 6 is the system of example 5 that may optionally include that compressed image pixel data associated with an image that is part of a series selected for display on the display has a higher priority and is requested before compressed image pixel data associated with an image that is not part of the series selected for display on the display.

Example 7 is the system of example 1 that may optionally include that the processor is operable to request compressed image pixel data from an image cache over requesting the compressed image pixel data from a server remotely located from the server in order to compensate for a low network speed environment in which network speed is below a threshold.

Example 8 is the system of example 1 that may optionally include that the image comprises a DICOM image.

Example 9 is the system of example 1 that may optionally include that the processor is operable to download compressed image data to the image cache as a background process before the study is opened for review.

Example 10 is the system of example 1 that may optionally include that the viewer is part of a browser.

Example 11 is a method for displaying images from a healthcare study in a graphical user interface (GUI), the method comprising: determining whether compressed image pixel data associated with an image of a healthcare study selected for display is in an image cache memory of a medical image management system; if the compressed image pixel data associated with an image of a healthcare study selected for display is in an image cache memory of a medical image management system, then fetching the compressed image pixel data from an image cache, the image pixel data representing a pre-rendered version of an image from a series in the healthcare study, decompressing the compressed image pixel data to obtain the image pixel data, performing one or more image processing operations on the image pixel data, generating a displayable image from the image pixel data that has undergone image processing, and rendering the displayable image for display with a viewer on the display, and if the compressed image pixel data associated with an image of a healthcare study selected for display is not in an image cache memory of a medical image management system, then downloading from a remote location a version of the displayable image for display with the viewer; and displaying the displayable image with a viewer.

Example 12 is the method of example 11 that may optionally include requesting compressed image pixel data from a server remotely located with respect to the system via the network connection and downloading the compressed image pixel data into the image cache.

Example 12 is the method of example 11 that may optionally that downloading from a remote location a rendered version of the displayable image for display with the viewer comprises: generating and queuing the request at the medical image management system in response to the study being opened; sending, by a loader of the medical image management system, the request to the remotely located server; receiving and storing in the image cache, by the medical image management system, the compressed image pixel data received from the remotely located server.

Example 14 is the method of example 11 that may optionally that the compressed image pixel data is fetched based on a priority.

Example 15 is the method of example 14 that may optionally that compressed image pixel data associated with an image that is part of a series selected for display on the display has a higher priority and is requested before compressed image pixel data associated with an image that is not part of the series selected for display on the display.

Example 16 is the method of example 11 that may optionally that the image comprises a DICOM image.

Example 17 is the method of example 11 that may optionally that the viewer is part of a browser.

Example 18 is a non-transitory computer readable storage media having instructions stored thereupon which, when executed by a system having at least a processor and a memory therein, cause the system to perform a method for displaying images from a healthcare study in a graphical user interface (GUI), wherein the method comprises: determining whether compressed image pixel data associated with an image of a healthcare study selected for display is in an image cache memory of a medical image management system; if the compressed image pixel data associated with an image of a healthcare study selected for display is in an image cache memory of a medical image management system, then fetching the compressed image pixel data from an image cache, the image pixel data representing a pre-rendered version of an image from a series in the healthcare study, decompressing the compressed image pixel data to obtain the image pixel data, performing one or more image processing operations on the image pixel data, generating a displayable image from the image pixel data that has undergone image processing, and rendering the displayable image for display with a viewer on the display; if the compressed image pixel data associated with an image of a healthcare study selected for display is not in an image cache memory of a medical image management system, then downloading from a remote location a version of the displayable image for display with the viewer; and displaying the displayable image with a viewer.

Example 19 is the computer readable storage media of example 18 that may optionally that the method further comprises requesting compressed image pixel data from a server remotely located with respect to the system via the network connection and downloading the compressed image pixel data into the image cache.

Example 20 is the computer readable storage media of example 19 that may optionally that downloading from a remote location a rendered version of the displayable image for display with the viewer comprises: generating and queuing the request at the medical image management system in response to the study being opened; sending, by a loader of the medical image management system, the request to the remotely located server; receiving and storing in the image cache, by the medical image management system, the compressed image pixel data received from the remotely located server.

Some portions of the detailed descriptions above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present invention also relates to apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the invention as described herein.

A machine-readable medium includes any mechanism for storing or transmitting information in a form readable by a machine (e.g., a computer). For example, a machine-readable medium includes read only memory ("ROM"); random access memory ("RAM"); magnetic disk storage media; optical storage media; flash memory devices; electrical, optical, acoustical or other form of propagated signals (e.g., carrier waves, infrared signals, digital signals, etc.); etc.

Whereas many alterations and modifications of the present invention will no doubt become apparent to a person of ordinary skill in the art after having read the foregoing description, it is to be understood that any particular embodiment shown and described by way of illustration is in no way intended to be considered limiting. Therefore, references to details of various embodiments are not intended to limit the scope of the claims which in themselves recite only those features regarded as essential to the invention.

We claim:

1. A system comprising:
   a network communication interface to receive compressed image pixel data;
   an image cache memory to cache the compressed DICOM image pixel data and rendered images;
   one or more processors coupled to the network connection interface and the memory and configured to implement an image rendering pipeline to perform image rendering in response to opening a healthcare study for review, wherein the image rendering includes determining whether compressed image pixel data associated with an image selected for display is in an image cache memory, and if so, then
      fetching the compressed image pixel data from an image cache, the image pixel data representing a pre-rendered version of an image from a series in the healthcare study,
      decompressing the compressed image pixel data to obtain the image pixel data,
      performing one or more image processing operations on the image pixel data,
      generating a displayable image from the image pixel data that has undergone image processing, and
      rendering the displayable image for display with a viewer on the display, and if not, then downloading from a remote location a version of the displayable image for display with the viewer;
   a display coupled to the one or more processors to display the displayable image with the viewer.

2. The system defined in claim 1 wherein the processor is further operable to request compressed image pixel data from a server remotely located with respect to the system via the network connection and download the compressed image pixel data into the image cache.

3. The system defined in claim 2 wherein the processor is further operable to:
   generate and queue the request in response to the healthcare study being opened;
   send, using a loader, the request to the remotely located server; and
   receive and store in the image cache the compressed image pixel data received from the remotely located server.

4. The system defined in claim 3 wherein the processor requests the compressed image pixel data from the server in response to determining the compressed image pixel data is not stored in the image cache.

5. The system defined in claim 4 wherein the compressed image pixel data is requested by the processor based on a priority.

6. The system defined in claim 5 wherein compressed image pixel data associated with an image that is part of a series selected for display on the display has a higher priority and is requested before compressed image pixel data associated with an image that is not part of the series selected for display on the display.

7. The system defined in claim 1 wherein the processor is operable to request compressed image pixel data from an image cache over requesting the compressed image pixel data from a server remotely located from the server in order to compensate for a low network speed environment in which network speed is below a threshold.

8. The system defined in claim 1 wherein the image comprises a DICOM image.

9. The system defined in claim 1 wherein the processor is operable to download compressed image data to the image cache as a background process before the study is opened for review.

10. The system defined in claim 1 wherein the viewer is part of a browser.

11. A method for displaying images from a healthcare study in a graphical user interface (GUI), the method comprising:
    determining whether compressed image pixel data associated with an image of a healthcare study selected for display is in an image cache memory of a medical image management system;
    if the compressed image pixel data associated with an image of a healthcare study selected for display is in an image cache memory of a medical image management system, then
       fetching the compressed image pixel data from an image cache, the image pixel data representing a pre-rendered version of an image from a series in the healthcare study,
       decompressing the compressed image pixel data to obtain the image pixel data,
       performing one or more image processing operations on the image pixel data,
       generating a displayable image from the image pixel data that has undergone image processing, and
       rendering the displayable image for display with a viewer on the display;
    if the compressed image pixel data associated with an image of a healthcare study selected for display is not in an image cache memory of a medical image management system, then downloading from a remote location a version of the displayable image for display with the viewer; and
    displaying the displayable image with the viewer.

12. The method defined in claim 11 further comprising requesting compressed image pixel data from a server remotely located with respect to the system via the network connection and downloading the compressed image pixel data into the image cache.

13. The method defined in claim 12 wherein downloading from a remote location a rendered version of the displayable image for display with the viewer comprises:
    generating and queuing the request at the medical image management system in response to the study being opened;
    sending, by a loader of the medical image management system, the request to the remotely located server; and
    receiving and storing in the image cache, by the medical image management system, the compressed image pixel data received from the remotely located server.

14. The method defined in claim 11 wherein the compressed image pixel data is fetched based on a priority.

15. The method defined in claim 14 wherein compressed image pixel data associated with an image that is part of a series selected for display on the display has a higher priority and is requested before compressed image pixel data associated with an image that is not part of the series selected for display on the display.

16. The method defined in claim 11 wherein the image comprises a DICOM image.

17. The method defined in claim 11 wherein the viewer is part of a browser.

18. A non-transitory computer readable storage media having instructions stored thereupon which, when executed by a system having at least a processor and a memory therein, cause the system to perform a method for displaying images from a healthcare study in a graphical user interface (GUI), wherein the method comprises:
   determining whether compressed image pixel data associated with an image of a healthcare study selected for display is in an image cache memory of a medical image management system;
   if the compressed image pixel data associated with an image of a healthcare study selected for display is in an image cache memory of a medical image management system, then
      fetching the compressed image pixel data from an image cache, the image pixel data representing a pre-rendered version of an image from a series in the healthcare study,
      decompressing the compressed image pixel data to obtain the image pixel data,
      performing one or more image processing operations on the image pixel data,
      generating a displayable image from the image pixel data that has undergone image processing, and
      rendering the displayable image for display with a viewer on the display;
   if the compressed image pixel data associated with an image of a healthcare study selected for display is not in an image cache memory of a medical image management system, then downloading from a remote location a version of the displayable image for display with the viewer; and
   displaying the displayable image with the viewer.

19. The non-transitory computer readable storage media defined in claim 18 wherein the method further comprises requesting compressed image pixel data from a server remotely located with respect to the system via the network connection and downloading the compressed image pixel data into the image cache.

20. The non-transitory computer readable storage media defined in claim 19 wherein downloading from a remote location a rendered version of the displayable image for display with the viewer comprises:
   generating and queuing the request at the medical image management system in response to the study being opened;
   sending, by a loader of the medical image management system, the request to the remotely located server; and
   receiving and storing in the image cache, by the medical image management system, the compressed image pixel data received from the remotely located server.

* * * * *